US010076323B2

(12) United States Patent
Smith et al.

(10) Patent No.: US 10,076,323 B2
(45) Date of Patent: Sep. 18, 2018

(54) LONGITUDINAL NEEDLE PASSER

(71) Applicant: Boston Scientific Scimed, Inc., Maple Grove, MN (US)

(72) Inventors: Paul Smith, Smithfield, RI (US); Justin Elfman, Cherry Hill, NJ (US); Samuel Raybin, Marlborough, MA (US); Liam K. P. M. Rolle, Boston, MA (US); Naroun Suon, Lawrence, MA (US); John B. Golden, Norton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 342 days.

(21) Appl. No.: 14/842,417

(22) Filed: Sep. 1, 2015

(65) Prior Publication Data
US 2016/0066902 A1 Mar. 10, 2016

Related U.S. Application Data

(60) Provisional application No. 62/048,449, filed on Sep. 10, 2014.

(51) Int. Cl.
*A61B 17/04* (2006.01)
*A61B 17/062* (2006.01)
*A61B 17/06* (2006.01)

(52) U.S. Cl.
CPC .. *A61B 17/0625* (2013.01); *A61B 2017/0417* (2013.01); *A61B 2017/0609* (2013.01); *A61B 2017/06047* (2013.01)

(58) Field of Classification Search
CPC ........ A61B 17/0625; A61B 2017/0417; A61B 2017/06047; A61B 2017/0609
See application file for complete search history.

(56) References Cited

U.S. PATENT DOCUMENTS

2009/0177031 A1* 7/2009 Surti ................. A61B 1/00087
600/106
2012/0277768 A1* 11/2012 Viola ................ A61B 17/0469
606/145

FOREIGN PATENT DOCUMENTS

| DE | 41 24 381 | 8/1992 |
| JP | 2007275577 | 10/2007 |
| JP | 2011509121 | 3/2011 |

* cited by examiner

*Primary Examiner* — Julie A Szpira
(74) *Attorney, Agent, or Firm* — Fay Kaplun & Marcin, LLP

(57) ABSTRACT

A device for passing a needle and suture longitudinally through a target tissue includes a proximal jaw including a proximal recess and a proximal retention mechanism for releasably engaging a first end of a needle received within the proximal recess and a distal jaw movably coupled to the proximal jaw such that the proximal and distal jaws are longitudinally movable relative to one another. The distal jaw includes a distal recess and a distal retention mechanism for releasably engaging a second end of the needle received within the distal recess. The proximal and distal jaws are movable between a first state, in which the proximal retention mechanism is in a locked configuration and the distal retention mechanism is in an unlocked configuration, and a second state, in which the proximal retention mechanism is in an unlocked configuration and the distal retention mechanism is in a locked configuration.

13 Claims, 6 Drawing Sheets

LONGITUDINAL NEEDLE PASSER

PRIORITY CLAIM

The present disclosure claims priority to U.S. Provisional Patent Application Ser. No. 62/048,449 filed Sep. 10, 2014; the disclosure of which is incorporated herewith by reference.

BACKGROUND

Physicians have been increasingly willing to perform more aggressive interventional and therapeutic endoscopic procedures including, for example, the removal of larger lesions (e.g., cancerous masses), tunneling under the mucosal layer of the gastrointestinal (GI) tract to treat tissue below the mucsoa, full thickness removal of tissue, the treatment of issues on other organs by penetrating and passing of the GI tract, and the endoscopic treatment/repair of post-surgical issues (e.g., post-surgical leaks, breakdown of surgical staple lines, anastomic leaks). These procedures my increase the risk of perforating the wall of the GI tract, or may require closure of the GI tract wall as part of the procedure. Endoscopic closure can save costs for the hospital and provide benefits to the patient. Conventional devices for tissue closure may be difficult to use and time consuming in certain conditions. In addition, conventional devices may be insufficient to close certain perforations or to treat certain conditions and anatomies such as, for example, large wounds created in the GI tract.

SUMMARY

The present disclosure is directed to a device for passing a needle and suture longitudinally through a target tissue, comprising a proximal jaw including a proximal recess extending through a distal surface thereof and a proximal retention mechanism for releasably engaging a first end of a needle received within the proximal recess and a distal jaw movably coupled to the proximal jaw such that the proximal and distal jaws are longitudinally movable relative to one another, the distal jaw including a distal recess extending through a proximal surface thereof and a distal retention mechanism for releasably engaging a second end of the needle received within the distal recess, the proximal and distal jaws movable between a first state, in which the proximal retention mechanism is in a locked configuration to engage a needle received in the proximal recess and the distal retention mechanism is in an unlocked configuration so that a needle received in the distal recess is freely slidable therethrough, and a second state, in which the proximal retention mechanism is in an unlocked configuration so that a needle received in the proximal recess is freely slidable therethrough and the distal retention mechanism is in a locked configuration to engage a needle received in the distal recess.

At least one of the proximal retention mechanism and the distal retention mechanism may be a passively actuated retention mechanism.

The proximal retention mechanism may include a proximal wedge plate including an opening extending therethrough, the opening being substantially aligned with the proximal recess in the unlocked configuration and being angled with respect to the proximal recess in the locked configuration.

The distal retention mechanism may include a ball detent extending into the distal recess and movable relative thereto.

A force of the proximal wedge plate in the locked configuration may be greater than a force of the ball detent in the locked configuration.

The distal retention mechanism may include a form spring including an engaging portion extending into the distal recess in the locked configuration and being deformable thereoutof in the unlocked configuration.

The device may further comprise a key movable relative to the proximal jaw to move the form spring between the locked and unlocked configuration.

The distal retention mechanism may include a distal wedge plate including an opening extending therethrough, the opening being substantially aligned with the distal recess in the unlocked configuration and angled relative to the distal recess in the locked configuration.

The distal retention mechanism may include a control member longitudinally movable relative to the distal jaw, a distal end of the control member extending into the distal recess in the locked configuration.

The present disclosure also relates to a system for treating a tissue opening, comprising a needle extending from a first end to a second end, a suture extending from a distal end connected to the needle between the first and second ends to a proximal end, and a delivery device for delivering the needle and suture through a target tissue, including a proximal jaw including a proximal recess extending through a distal surface thereof and a proximal retention mechanism for releasably engaging the first end of the needle in the proximal recess and a distal jaw movably coupled to the proximal jaw such that the proximal and distal jaws are longitudinally movable relative to one another to receive a target tissue therebetween, the distal jaw including a distal recess extending through a proximal surface thereof and a distal retention mechanism for releasably engaging the second end of the needle in the distal recess, the proximal and distal jaws movable between a first state, in which the proximal retention mechanism is in a locked configuration to engage the needle received in the proximal recess and the distal retention mechanism is in an unlocked configuration so that the needle is freely slidable through the distal recess, and a second state, in which the proximal retention mechanism is in an unlocked configuration so that the needle is freely slidable through the proximal recess and the distal retention mechanism is in a locked configuration to engage a needle received in the distal recess.

At least one of the first end and the second end may include a first groove extending thereabout for engaging a portion of the proximal retention mechanism in the locked configuration.

The proximal retention mechanism may include a proximal wedge plate including an opening extending therethrough, the opening being substantially aligned with the proximal recess in the unlocked configuration and being angled with respect to the proximal recess in the locked configuration.

The distal retention mechanism may include a ball detent extending into the distal recess in the locked configuration and movable thereoutof in the unlocked configuration.

The distal retention mechanism may include a form spring including an engaging portion extending into the distal recess in the locked configuration and being deformable thereoutof in the unlocked configuration.

The distal retention mechanism may include a distal wedge plate including an opening extending therethrough, the opening being substantially aligned with the distal recess in the unlocked configuration and angled relative to the distal recess in the locked configuration.

The present disclosure also relates to a method for treating a tissue defect, comprising inserting a device to a target area within a patient body via a working channel of an endoscope, inserting a distal portion of the device through a tissue opening to be treated so that a proximal jaw of the device is positioned proximally of a proximal surface of a target tissue about a periphery of the tissue opening and a distal jaw of the device is positioned distally of a distal surface of the target tissue, moving the distal and proximal jaws longitudinally toward one another such that a needle locked within a proximal recess of the proximal jaw via a proximal retention mechanism locking a first end of the needle is passed through a first portion of the target tissue from the proximal surface to the distal surface thereof until a second end of the needle is received within a distal recess in the distal jaw, unlocking the proximal retention mechanism so that the first end of the needle is released therefrom and the second end of the needle engages the distal retention mechanism, and moving the distal and proximal jaws longitudinally away from one another such that the needle extends distally past the distal surface of the target tissue, threading a suture attached to the needle through the first portion of the target tissue.

DETAILED DESCRIPTION

Figure 1:
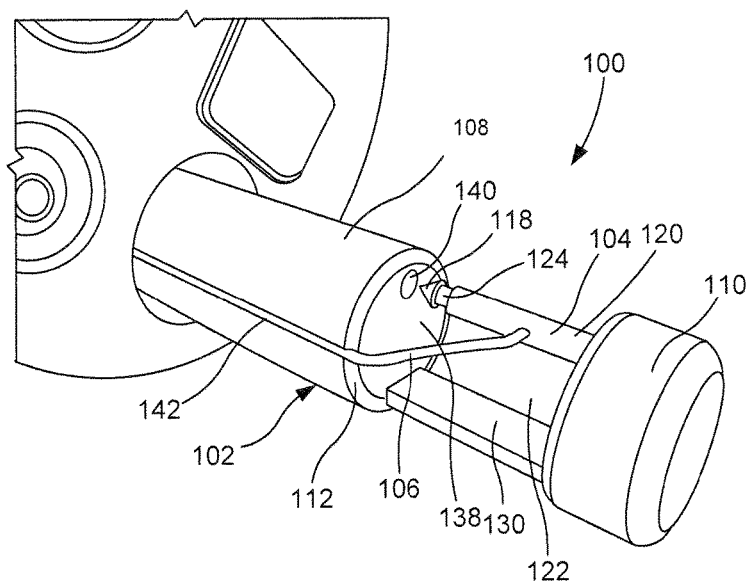
FIG. 1 shows a perspective view of a system according to a first exemplary embodiment of the present disclosure.
Figure 2:
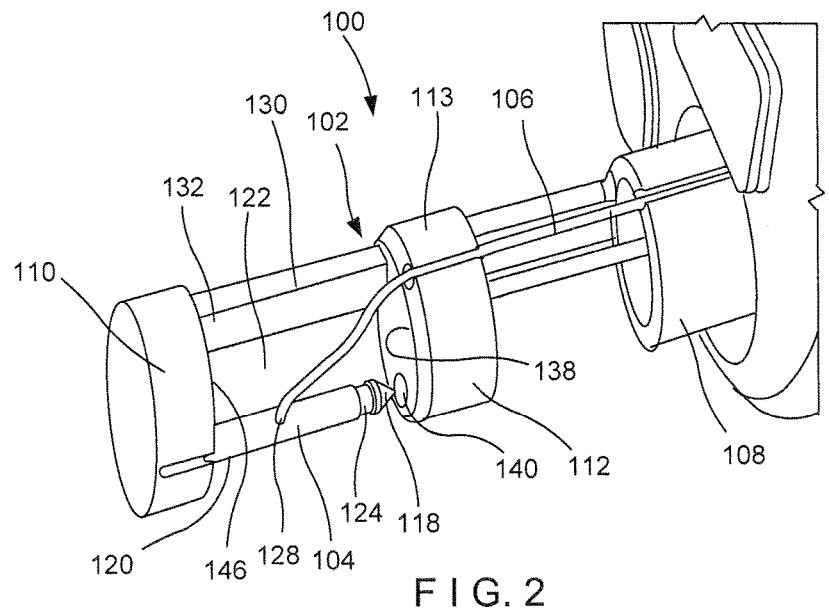
FIG. 2 shows another perspective view of the system of FIG. 1.
Figure 3:
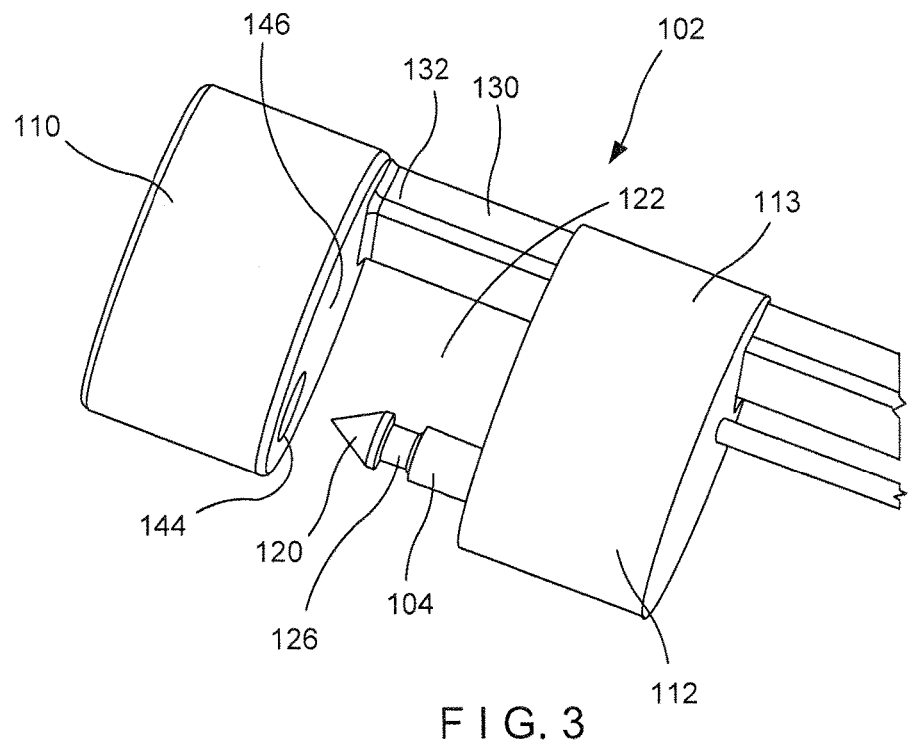
FIG. 3 shows a perspective view of a distal portion of a delivery device of the system of FIG. 1.

The present disclosure may be further understood with reference to the following description and the appended drawings, wherein like elements are referred to with the same reference numerals. The present disclosure is directed to devices for the treatment of tissue and, in particular endoscopic tissue treatment devices. Exemplary embodiments of the present disclosure describe a system for passing a needle and suture longitudinally through target tissue to close a tissue opening. In particular, the needle is passed longitudinally through the target tissue alternatingly between proximal and distal surfaces thereof to be threaded along about a periphery of the tissue opening. Once the needle and suture have been threaded about the entire tissue opening, the suture may be tensioned to cinch the tissue opening to a closed configuration. It should be noted that the terms "proximal" and "distal" are intended to refer to a direction toward (proximal) and away from (distal) a user of the device.

As shown in FIGS. 1-4, a system 100 according to a first exemplary embodiment of the disclosure comprises a delivery device 102 sized and shaped for insertion through an insertion device (e.g., through a working channel of an endoscope) to a target tissue site within a patient's body to pass a needle 104 and suture 106 longitudinally (i.e., distally and proximally) through the target tissue to thread the needle 104 and suture 106 along tissue extending about a periphery of a tissue opening to cinch the tissue opening closed. The delivery device 102 includes a longitudinal member 108 and a distal jaw 110 longitudinally movable relative thereto such that the target tissue may be received in a space 122 between a distal end 112 of the longitudinal member 108 and the distal jaw 110. The distal end 112 of the longitudinal member 108 includes a proximal retention mechanism 114 for releasably engaging a first end 118 of the needle 104 in a first configuration and the distal jaw 110 includes a distal retention mechanism 116 for releasably engaging a second end 120 of the needle 104 in a second configuration. In the first configuration, the needle 104 is engaged to the distal end 112 of the longitudinal member 108 and may be inserted through the target tissue received in the space 122 by moving the distal jaw 112 proximally relative to the longitudinal member 108. The proximal movement of the distal jaw 110 causes the needle 104 to be inserted through the target tissue from the proximal surface of the target to the distal surface of the target tissue, threading the suture 106 correspondingly therethrough. As the needle 104 is inserted through the target tissue, the needle 104 is moved to the second configuration in which the second end 120 of the needle 104 engages the distal retention mechanism 116. The distal jaw 112 is then moved distally relative to the longitudinal member 108 so that the first end 118 disengages the proximal retention mechanism 114 and the needle 104 is positioned distally of the target tissue received within the space 122. The needle 104 and suture 106 are then inserted through an adjacent portion of the target tissue along the periphery of the tissue opening from the distal surface to the proximal surface by once again moving the distal jaw 110 proximally relative to the longitudinal member 108. The needle 104 is then repositioned and alternatingly moved between the first and second configurations to be passed alternatingly through the target tissue between the proximal and distal surfaces until the entire periphery of the tissue opening has been threaded via the suture 106. Once the entire periphery of the tissue opening has been threaded, the needle 104 is released from the delivery device 102 so that the needle 104 acts as an anchor. The suture 106 may then be tensioned, drawing edges of the tissue opening together to close the tissue opening. The system 100 may further comprise a cinch (not shown) mountable over a portion of the suture 106 to lock the tensioned suture 106 at the desired tension and hold the tissue opening closed configuration. The system 100 may also comprise a handle assembly (not shown) at a proximal end of the delivery device 102, the handle assembly including actuators for moving the distal jaw 110 relative to the longitudinal member 108, releasing the proximal and distal retention mechanisms 114, 116, and tensioning the suture 106.

The needle 104 extends longitudinally from the first end 118 to the second end 120. Each of the first and second ends 118, 120 is tapered to facilitate piercing tissue as the needle 104 is passed therethrough in opposite directions. The first end 118 includes a first groove 124 extending along a portion thereof for engaging a portion of the proximal retention mechanism 114. The groove 124 may, for example, extend circumferentially about at least a portion of the first end 118. The second end 120 includes a second groove 126 extending along a portion thereof for engaging a portion of the distal retention mechanism. The second groove 126 may extend circumferentially about at least a portion of the second end 120. The suture 106 extends from a distal end 128 connected to the needle 104 between the proximal and distal ends 118, 120 thereof along a portion of the delivery device 102 to a proximal end accessible to a user of the delivery device 102 via, for example, the handle assembly.

The longitudinal member 108 extends longitudinally from a proximal end (not shown) to the distal end 112. A distal surface 138 of the distal end 112 may include a recess 140 extending therein, the recess 140 sized and shaped to receive the first end 118 of the needle 104 therein so that the first end 118 may engage a portion of the proximal retention mechanism 114 housed within the distal end 112 of the longitudinal member 108. The longitudinal member 108 may also include a longitudinal groove 142 extending along a length thereof for receiving a portion of the suture 106 therein. The suture 106 may extend along the longitudinal member 108 along the longitudinal groove 142 to the proximal end.

The distal jaw 110 may be movably coupled to the longitudinal member 108 via a connecting rod 130. A distal end 132 of the connecting rod 130 is fixed to the distal jaw 110 while a length of the connecting rod 130 extends through a wall of the longitudinal member 108 to a proximal end accessible to the user. Thus, the connecting rod 130 may be moved longitudinally relative to the longitudinal member 108 to move the distal jaw 110 proximally and distally relative to the longitudinal member 108. In particular, moving the connecting rod 130 distally relative to the longitudinal member 108 moves the distal jaw 110 away from the distal end 112 of the longitudinal member 108, increasing the size of the space 122 therebetween.

Moving the connecting rod 130 proximally relative to the longitudinal member 108 moved the distal jaw 110 toward the distal end 112 of the longitudinal member 108, decreases the size of the space 122. The distal jaw 110 also includes a recess 144 extending through a proximal surface 146 thereof configured to receive the second end 120 of the needle 104 therein so that it may engage a portion of the distal retention mechanism 116. The recess 140 in the distal end 112 of the longitudinal member 108 and the recess 144 in the distal jaw 144 are aligned with one another so that a needle 104 may be moved between the first and second configurations, as described above. In one exemplary embodiment, the recesses 140, 144 extend through portions of the distal end 112 of the longitudinal member 108 and the distal jaw 110, respectively, substantially opposing the connecting rod 130.

Figure 4:
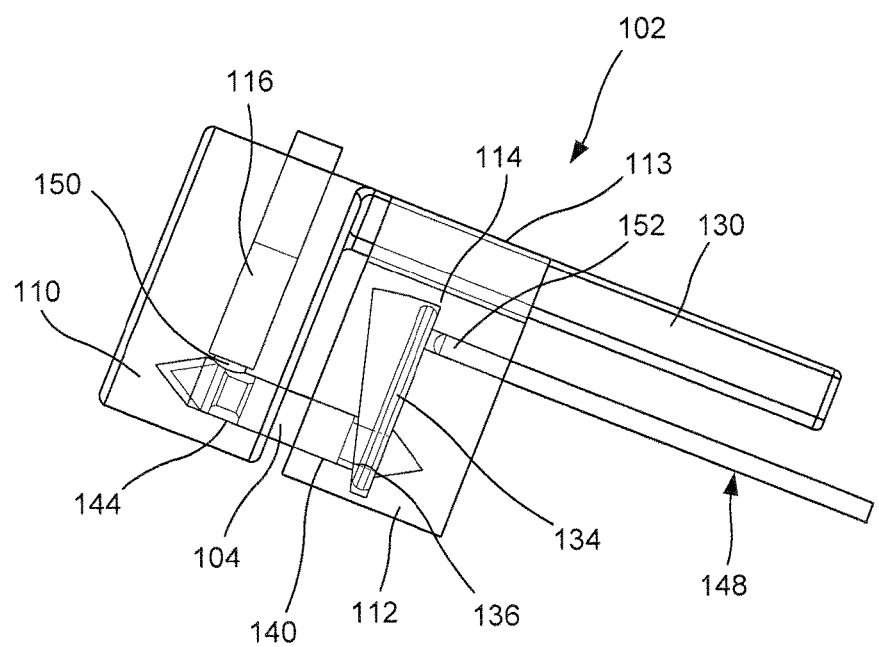
FIG. 4 shows a transparent side view of the distal portion of the delivery device of FIG. 3.

As shown in FIG. 4, the proximal retention mechanism 114 according to this embodiment includes a wedge plate 134. The wedge plate 134 is movably housed within the distal end 112 of the longitudinal member 108 and is movable between an unlocked configuration, in which the wedge plate 134 extends substantially parallel to a distal surface 138 of the longitudinal member 108 (e.g., substantially perpendicular to a longitudinal axis of the delivery device 102), and a locked configuration, in which the wedge plate 134 is angled relative to the distal surface 138. The wedge plate 134 includes an opening 136 extending therethrough sized and shaped to permit the first end 118 of the needle 104 to pass freely therethrough when the wedge plate 134 is in the unlocked configuration. For example, the opening 136 may be substantially circular, having a diameter larger than a diameter of the needle 104. In the unlocked configuration, the opening 136 is substantially aligned with the recess 140 so that the needle 104 does not engage any portion thereof. When the wedge plate 134 is moved to the locked configuration, however, the opening 136 is angled causing an edge of the opening 136 to engage the first groove 124, locking the needle 104 in the distal end 112 of the longitudinal member 108.

The wedge plate 134 in this embodiment is moved between the unlocked and locked configurations via a control element 148 extending from a distal end 152 connected to the wedge plate 134 to a proximal end which remains outside the body accessible by the user. The proximal end of the control element 148 may, for example, be connected to an actuator of the handle assembly. The control element 148 is moved longitudinally relative to the longitudinal member 108 to move the wedge plate 134 between the unlocked and locked configurations. The control element 148 may, for example, be moved distally relative to the longitudinal member 108 to move the wedge plate 134 to the locked configuration and proximally relative to the longitudinal member 108 to move the wedge plate 134 to the unlocked configuration. In another embodiment, the movement of the control element 148 may be reversed. For example, the control element 148 may be moved distally relative to the longitudinal member 108 to move the wedge plate 134 to the unlocked configured and proximally relative to the longitudinal member 108 to move the wedge plate 134 to the locked configuration.

The distal retention mechanism 116 according to this embodiment includes a ball detent 150 within the distal jaw 110 so that a portion of the ball 150 extends into the recess 144. Thus, when the second end 120 of the needle 104 is received within the recess 144, the ball 150 engages the second groove 126, holding the needle 104 within the recess 144. The wedge plate 134 of the proximal retention mechanism 114 provides a greater force than the ball detent 150, however, so that when the first end 118 of the needle 104 is locked via the wedge plate 134, the second end 120 of the needle 104 maybe pulled out of engagement with the ball detent 150. The distal retention mechanism 116, however, may be any passively actuated lock mechanism (e.g., mechanism that does not require any user interface) which permits the needle 104 to be locked/unlocked within the recess 144 when the needle 104 is inserted into/removed from the distal recess 144 with sufficient force.

According to an exemplary method using the system 100, the delivery device 102 is inserted through an insertion device such as a working channel of an endoscope to a target tissue site within a living body. The exemplary method will be described with the delivery device 102 inserted through the working channel with the needle 104 in the first configuration (i.e., with the first end 118 of the needle 104 engaging the proximal retention mechanism 114). However, the delivery device 102 may be similarly inserted through the working channel with the needle 104 in the second configuration (i.e., the second end 120 of the needle 104 engaging the distal retention mechanism 116). Once inserted through the working channel to the target tissue site, the delivery device 102 is positioned such that a first portion of the target tissue extending about a periphery of a tissue opening is received within the space 122 between the distal end 112 of the longitudinal member 108 and the distal jaw 110. More particularly, the tissue is received between the distal jaw 110 and the needle 104 extending from the distal end 112 of the longitudinal member 108. The distal jaw 110 is then moved proximally relative to the longitudinal member 108 so that the needle 104 is inserted through the first portion of tissue and the second end 120 of the needle 104 is received within the recess 144 of the distal jaw 110 so that the second end 120 engages the ball detent 150. The wedge plate 134 of the proximal retention mechanism 114 is moved from the locked to the unlocked configuration via the control element 148, releasing the first end 118 of the needle 104 from the distal end 112 of the longitudinal member 108, so that the distal jaw 110 may be moved distally away from the longitudinal member 108 with the needle 104 engaging the distal jaw 110. As the distal jaw 110 is moved distally relative to the longitudinal member 108, the needle 104 passes through the target issue to extend distally past the distal surface thereof, thereby threading the suture 106 through the first portion of tissue.

The delivery device 102 is then positioned over a second portion of the target tissue adjacent to the first portion about the periphery of the tissue opening so that the second portion of the target tissue is received within the space 120. More particularly, the second portion of tissue is received between the needle 104 and the distal end 112 of the longitudinal element 108. The distal jaw 110 is moved proximally relative to the longitudinal member 108 to insert the needle 104 through the second portion of tissue. The first end 118 of the needle 104 extends proximally past the proximal surface of the target tissue into the recess 140. The wedge plate 134 is then moved from the unlocked configuration to the locked configuration to lock the needle 104 therein. The distal jaw 110 is again moved distally relative to the longitudinal member 108. Since the force of the wedge plate 134 is greater than the force of the ball detent 150, moving the distal jaw 110 distally disengages the needle 104 from the distal jaw 110 so that the needle 104 extends proximally beyond the proximal surface of the target tissue, threading the suture 106 through the second portion of tissue.

The above-described steps are then repeated at different locations around the tissue opening until the suture 106 has been threaded through a desired set of locations around the tissue opening. In particular, the needle 104 is moved between the first and second configurations, alternatingly passing through the proximal and distal surfaces of the target tissue. Once the suture 106 has been threaded about an entire periphery of the tissue opening, the needle 104 is released from the delivery device 102. The needle 104 may be released when the needle 104 is in the first configuration and the distal jaw 110 and the distal end 112 of the longitudinal member 108 are separated from one another. To release the needle 104, the wedge plate 134 is moved to the unlocked configuration, permitting the needle 104 to freely disengage from the opening 136 and be released from the recess 140 at the distal end 112. Once the needle 104 has been released from the delivery device 102, the needle 104 acts as a T-tag anchor, rotating about the point at which the needle 104 is connected to the suture 106 so that a length of the needle 104 extends substantially perpendicular to a length of the suture 106. Thus, when tension is applied to the suture 106 by drawing the suture 106 proximally relative to the longitudinal member 108, the needle 104 becomes anchored in a portion of the target tissue and edges of the tissue opening are drawn toward one another to close the tissue opening. The tissue opening may be fixed in the closed configuration via a cinch applied to the suture 106, as would be understood by those skilled in the art.

As described above, the distal end 112 of the longitudinal member 108 acts substantially as a proximal jaw 113. Although the system 100 has been described as including a delivery device 102 with the proximal retention mechanism 114 in the distal end 112 of the longitudinal member 108, the delivery device 102 may include a separate proximal jaw 113 including the proximal retention mechanism 114 coupled to the distal end 112 of the longitudinal member 108. In addition, although the system 100 shows and describes the distal end 112 (e.g., proximal jaw 113) as remaining stationary while the distal jaw 110 is moved longitudinally relative thereto, the distal jaw 110 may remain substantially stationary while a proximal jaw 113 including a proximal retention mechanism 114 is moved longitudinally relative thereto.

Figure 5:
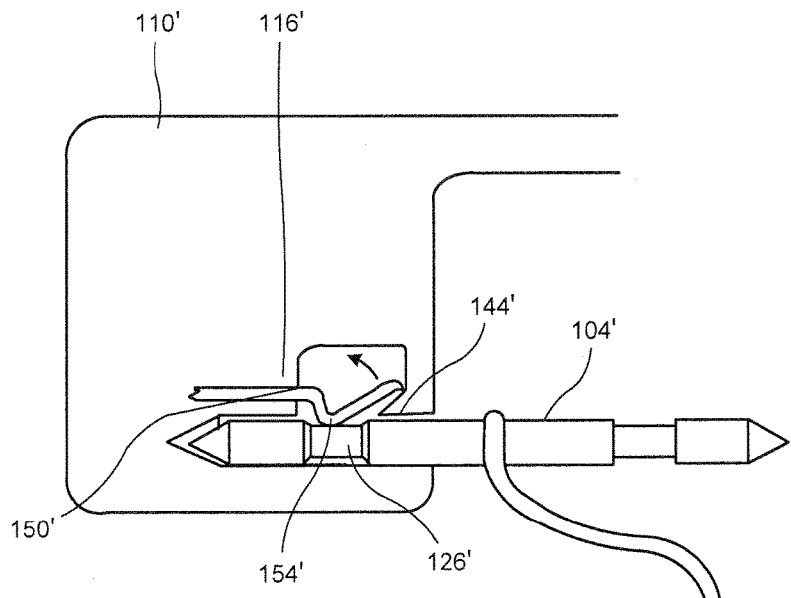
FIG. 5 shows a longitudinal cross-sectional view of a distal portion of a delivery device according to another embodiment of the present disclosure.

According to another embodiment, as shown in FIG. 5, rather than a ball detent as described above, a distal retention mechanism 116' of a distal jaw 110' may include a formed spring 150' housed therein with an engaging portion 154' of the formed spring extending into a recess 144' in an engaging configuration to engage the groove 126' of the needle 104. The formed spring 150' may be biased toward the engaging configuration while remaining deformable via longitudinal movement of a needle 104' so that the engaging portion 154' may be moved out of the recess 144'.

Figure 6:
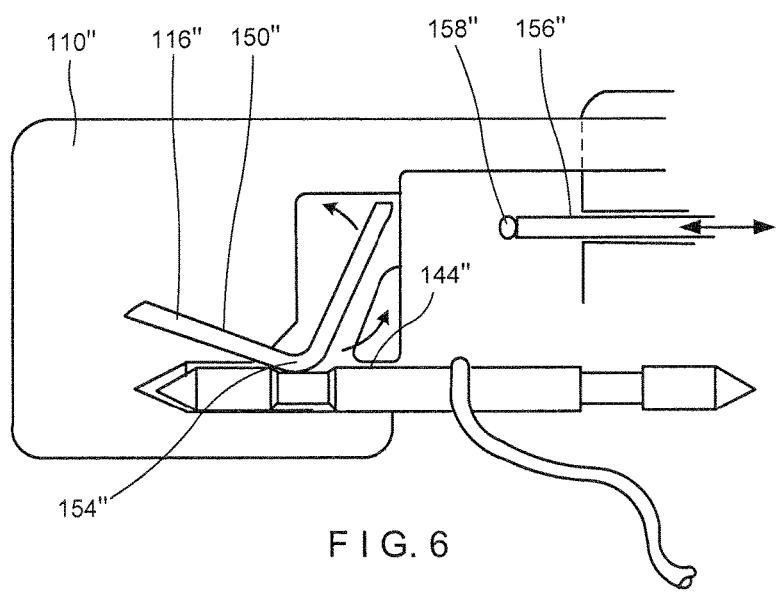
FIG. 6 shows a longitudinal cross-sectional view of a distal portion of a delivery device according to another embodiment of the present disclosure.

According to another embodiment, as shown in FIG. 6, a distal retention mechanism 116" is substantially similar to the distal retention mechanism 116', except as noted below, including a formed spring 150" with an engaging portion 154" thereof extending into a recess 144" in an engaging configuration. The formed spring 150", however, is moved from the engaging configuration to a disengaging configuration via, for example, a key element 156" movably extending from a distal end of a longitudinal member. The key element 156" is moved distally relative to the longitudinal element 108" so that a distal end 158" of the key element 156" extends into the distal jaw 110" to contact a portion of the formed spring 150", bending the formed spring 150" to move the engaging portion 154" out of the recess 144" in the disengaging configuration.

Figure 7:
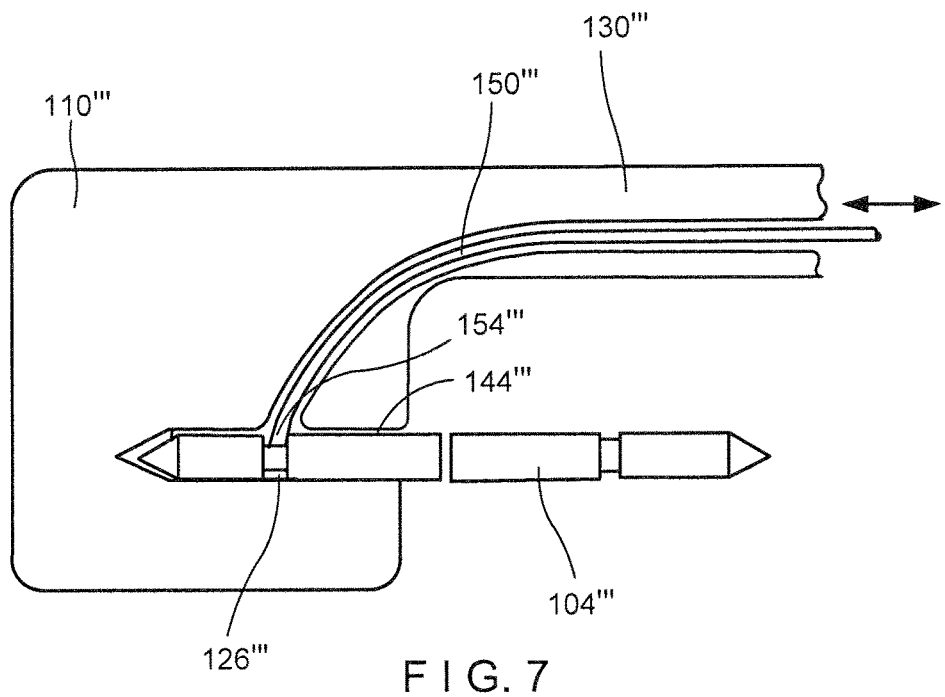
FIG. 7 shows a longitudinal cross-sectional view of a distal portion of a delivery device according to yet another embodiment of the present disclosure.

In another embodiment, as shown in FIG. 7, a distal retention mechanism 116''' includes a control element 150''' extending through the distal jaw 110''' so that a distal end 154''' of the control element 150''' extends into the recess 144''' to engage the first groove 126''' of the needle 104''' in the engaging configuration. The control element 150''' in this embodiment extends into the distal jaw 110''' via, for example, a connecting rod 130''' so that a proximal end thereof is accessible to a user via, for example, the handle assembly connected to the proximal end of the delivery device. To move the distal retention mechanism 116''' to the disengaging configuration, the control element 150''' is moved proximally relative to the delivery device 102 to move the distal end 154''' of the control element 150''' out of the recess 144'''.

Figure 8:
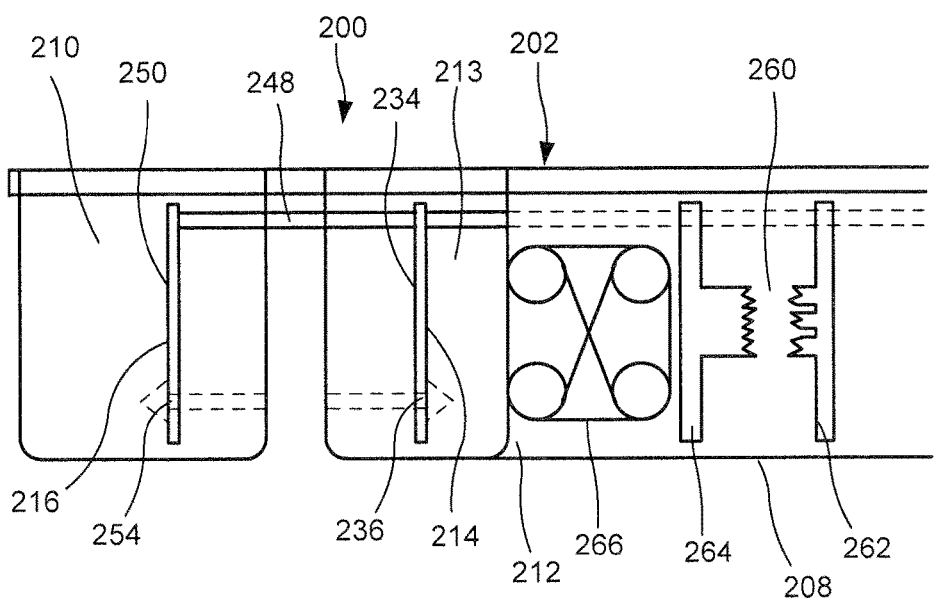
FIG. 8 shows a schematic side view of a system according to a second exemplary embodiment of the present disclosure.

As shown in FIG. 8, a system 200 according to another exemplary embodiment of the present disclosure is, except as noted below, similar to the system 100 described above, comprising a delivery device 202 for delivering a needle and suture longitudinally through target tissue. Similarly to the delivery device 102, the delivery device 202 includes a distal jaw 210 including a distal retention mechanism 216 and a distal end 212 of a longitudinal member 208 including a proximal retention mechanism 214. Similarly to the delivery device 102, the distal end 212 may include a separate proximal jaw 213 coupled thereto.

Similarly to the proximal retention mechanism 114, the proximal retention mechanism 214 includes a proximal wedge plate 234 including an opening 236 extending therethrough, the proximal wedge plate 234 being movable between unlocked and locked configurations. Rather than a ball detent, however, the distal retention mechanism 216 also includes a distal wedge plate 250 substantially similar to the wedge plates 134, 234, including an opening 254 extending therethrough. The distal wedge plate 250 is movable between unlocked and locked configurations. The proximal and distal wedge plates 234, 250 are movable between the unlocked and locked configurations via an angling thereof. The proximal and distal wedge plates 234, 250 are alternatingly movable between unlocked and locked configurations via an alternating mechanism 260. For example, when the alternating mechanism 260 is in a first position, the proximal wedge plate 234 is locked while the distal wedge plate 250 is unlocked.

When the alternating mechanism 260 is in a second position, the proximal wedge plate 234 is unlocked while the distal wedge plate 250 is locked.

The alternating mechanism 260 includes a distal cam 262 and a proximal cam 264 housed longitudinally within the longitudinal member 208, proximally of the proximal jaw 213 (e.g., proximally of the proximal wedge plate 234). A spring member 266 extends between the distal cam 262 and the proximal jaw 213. The alternating mechanism 260 is connected to the proximal and distal wedge plates 234, 250 via a control element 248 so that longitudinal movement of the distal jaw 210 and the proximal jaw 213 relative to one another causes the proximal and distal cams 262, 264 to interface with one another, toggling between the first and second positions described above.

Figure 9:
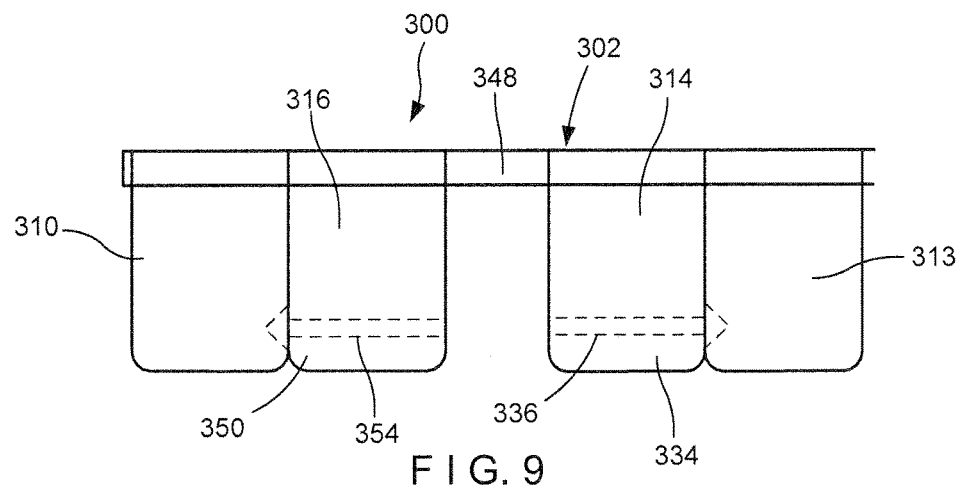
FIG. 9 shows a schematic side view of a system according to a third exemplary embodiment of the present disclosure.
Figure 10:
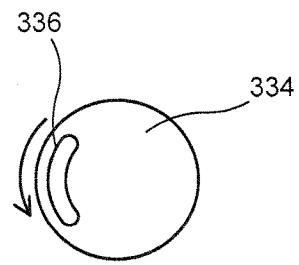
FIG. 10 shows a lateral cross-sectional view of a proximal retention mechanism of a delivery device of the system of FIG. 9.
Figure 11:
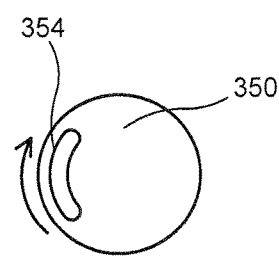
FIG. 11 shows a lateral cross-sectional side view of a distal retention mechanism of the delivery device of the system of FIG. 9.

As shown in FIGS. 9-11, a system 300 may be, except as noted below, substantially similar to the systems 100, 200 described above, comprising a delivery device 302 including a distal jaw 310 and a proximal jaw 313 movable longitudinally relative to one another to pass a needle and suture longitudinally through target tissue. A proximal retention mechanism 314 is coupled to a distal end of the proximal jaw 313 while a distal retention mechanism 316 is coupled to a proximal end of the distal jaw 310. As shown in FIG. 10, the proximal retention mechanism 314 includes a proximal disk 334 having a slot 336 extending longitudinally therethrough and elongated about a portion of the proximal disk 334 extending about a longitudinal axis of the delivery device 302. As shown in FIG. 11, the distal retention mechanism 316 includes a distal disk 350 having a slot 354 extending longitudinally therethrough and elongated about a portion of the distal disk 350 extending about the longitudinal axis of the delivery device 302. The proximal and distal disks 334, 350 are coupled to one another via a control element 348 which may be rotated to toggle the proximal and distal retention mechanisms 314, 316 between a first configuration, in which the proximal disk 334 is locked and the distal disk 350 is unlocked, and a second configuration, in which the proximal disk 334 is unlocked and the distal disk 350 is locked. In particular, the slots 336, 354 of the proximal and distal disks 334, 350, respectively, are offset from one another such that only a portion of each of the slots 336, 354 overlaps the other. Rotating the control element 348 correspondingly rotates the proximal and distal disks 334. For example, when the control element 348 is rotated in a first direction to the first configuration an edge of the slot 336 of the proximal disk 334 engages a needle received therewithin while the slot 354 of the distal disk 350 is positioned to permit the needle to freely slide therethrough. When the control element 348 is rotated in a second direction opposite the first direction to a second configuration, an edge of the slot 354 of the distal disk 350 engages the needle received therein while the slot 336 of the proximal disk 334 permits the needle to freely slide therein. Thus, the delivery device 302 may be toggled between the first and second configurations by rotating the control element 348.

Figure 12:
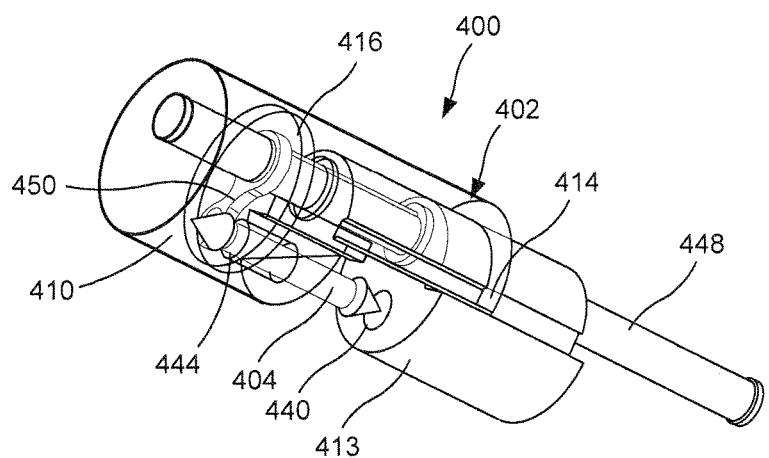
FIG. 12 shows a transparent perspective view of a system according to a fourth exemplary embodiment of the present disclosure.

As shown in FIG. 12, a system 400 may be, except as noted below, substantially similar to the system 300 described above and comprises a delivery device 402 including a proximal jaw 413 and a distal jaw 410 longitudinally movable relative to one another. Rather than disks, however, the proximal and distal retention mechanisms 414, 416 include a proximal paddle (not shown) and a distal paddle 450 (respectively). The proximal paddle is movably housed within the proximal jaw 413 on a first side of a recess 440 while the distal paddle 450 is movably housed within the distal jaw 410 on a second side of a recess 444 substantially opposite the first side. The proximal paddle and the distal paddle 450 are connected to one another via a control element 448 rotatable between a first configuration, in which the proximal paddle extends into the recess 440 of the proximal jaw 413 to engage a needle received therein while the distal paddle 450 does not extend into the recess 444 of the distal jaw 410, and a second configuration, in which the proximal paddle is moved out of the recess 440 while the distal paddle 450 extends into the recess 444 to engage the needle received therein. Thus, the delivery device 402 may be toggled between the first and second configurations via rotation of the control element 448.

Figure 13:
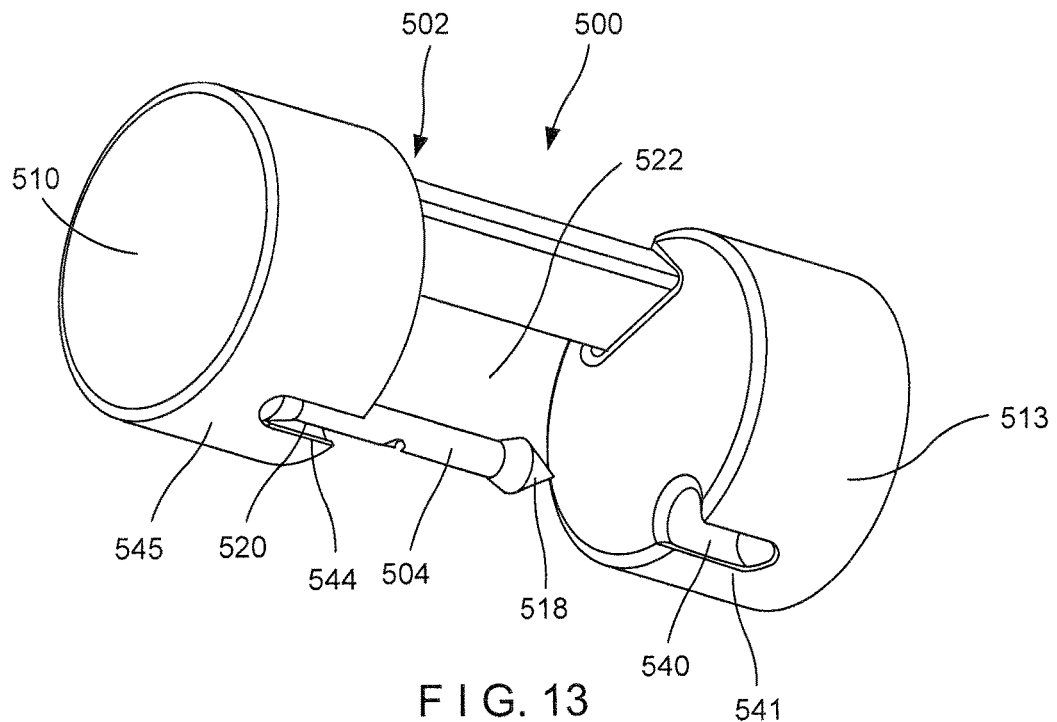
FIG. 13 shows a perspective view of a system according to a fifth exemplary embodiment of the present disclosure.

As shown in FIG. 13, a system 500 may be, except as noted below, substantially similar to the systems 100-400 described above, comprising a delivery device 502 including a distal jaw 510 and a proximal jaw 513 longitudinally movable relative to one another so that a needle 504 and suture may be longitudinally inserted through tissue received in a space 522 therebetween. To increase a width of the space 522 in which the target tissue may be received a recess 540 extending into the proximal jaw 513 for receiving a first end 518 of the needle 504 is open to a lateral surface 541 of the proximal jaw 513. Thus a wall of the recess 540 only extends about, for example a portion of a circumference thereof. A recess 544 extending into the distal jaw 510 for receiving a second end 520 of the needle 504 is open to a lateral surface 545 of the distal jaw 510 so that a wall of the recess 544 extends about only a portion of a circumference thereof.

Figure 14:
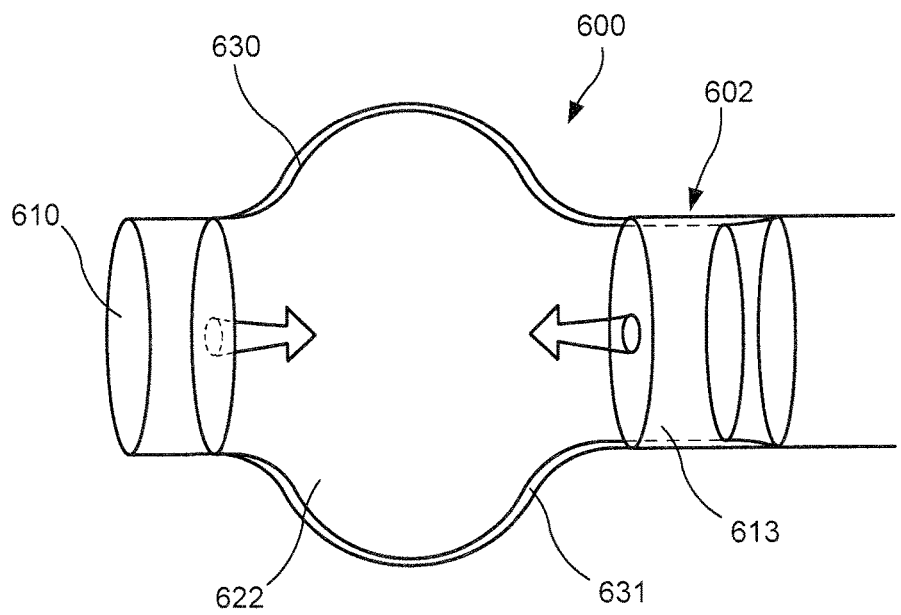
FIG. 14 shows a schematic side view of a system according to a sixth exemplary embodiment of the present disclosure.

As shown in FIG. 14, a system 600 may be, except as noted below, substantially similar to the system 500 described above and comprises a delivery device 602 including a distal jaw 610 and a proximal jaw 613 longitudinally movable relative to one another so that a needle and suture may be longitudinally inserted through a target tissue received within a space 622 extending therebetween. To increase a width of the space 622 so that a larger portion of the target tissue may be received therein, the distal and proximal jaws 610, 613 are connected to one another via first and second connecting members 630, 631. The first and second connecting members 630, 631 are substantially diametrically opposed to one another and are formed of a deformable material so that, when the distal and proximal jaws 610, 613 are moved longitudinally toward one another, the first and second connecting members 630, 631 deform, increasing the width (e.g., a distance between the first and second connecting members 630, 631).

It will be apparent to those skilled in the art that various modifications may be made in the present disclosure, without departing from the scope of the disclosure. Thus, it is intended that the present disclosure cover modifications and variations of this disclosure provided that they come within the scope of the appended claims and their equivalents.

What is claimed is:

1. A device for passing a needle and suture longitudinally through a target tissue, comprising:
   a proximal jaw including a proximal recess extending through a distal surface thereof and a proximal retention mechanism for releasably engaging a first end of a needle received within the proximal recess; and
   a distal jaw movably coupled to the proximal jaw such that the proximal and distal jaws are longitudinally movable relative to one another, the distal jaw including a distal recess extending through a proximal surface thereof and a distal retention mechanism for releasably engaging a second end of the needle received within the distal recess, the proximal and distal jaws movable between a first state, in which the proximal retention mechanism is in a locked configuration to engage a needle received in the proximal recess and the distal retention mechanism is in an unlocked configuration so that a needle received in the distal recess is freely slidable therethrough, and a second state, in which the proximal retention mechanism is in an unlocked configuration so that a needle received in the proximal recess is freely slidable therethrough and the distal retention mechanism is in a locked configuration to engage a needle received in the distal recess,
   wherein the proximal retention mechanism includes a proximal wedge plate including an opening extending therethrough, the opening being substantially aligned with the proximal recess in the unlocked configuration and being angled with respect to the proximal recess in the locked configuration.

2. The device of claim 1, wherein at least one of the proximal retention mechanism and the distal retention mechanism is a passively actuated retention mechanism.

3. The device of claim 1, wherein the distal retention mechanism includes a form spring including an engaging portion extending into the distal recess in the locked configuration and being deformable thereoutof in the unlocked configuration.

4. The device of claim 3, further comprising a key movable relative to the proximal jaw to move the form spring between the locked and unlocked configuration.

5. The device of claim 1, wherein the distal retention mechanism includes a distal wedge plate including an opening extending therethrough, the opening being substantially aligned with the distal recess in the unlocked configuration and angled relative to the distal recess in the locked configuration.

6. The device of claim 1, wherein the distal retention mechanism includes a control member longitudinally movable relative to the distal jaw, a distal end of the control member extending into the distal recess in the locked configuration.

7. A device for passing a needle and suture longitudinally through a target tissue, comprising:
   a proximal jaw including a proximal recess extending through a distal surface thereof and a proximal retention mechanism for releasably engaging a first end of a needle received within the proximal recess; and
   a distal jaw movably coupled to the proximal jaw such that the proximal and distal jaws are longitudinally movable relative to one another, the distal jaw including a distal recess extending through a proximal surface thereof and a distal retention mechanism for releasably engaging a second end of the needle received within the distal recess, the proximal and distal jaws movable between a first state, in which the proximal retention mechanism is in a locked configuration to engage a needle received in the proximal recess and the distal retention mechanism is in an unlocked configuration so that a needle received in the distal recess is freely slidable therethrough, and a second state, in which the proximal retention mechanism is in an unlocked configuration so that a needle received in the proximal recess is freely slidable therethrough and the distal retention mechanism is in a locked configuration to engage a needle received in the distal recess, wherein the distal retention mechanism includes a ball detent extending into the distal recess and movable relative thereto.

8. The device of claim 7, wherein a force of the proximal wedge plate in the locked configuration is greater than a force of the ball detent in the locked configuration.

9. A system for treating a tissue opening, comprising:
   a needle extending from a first end to a second end;
   a suture extending from a distal end connected to the needle between the first and second ends to a proximal end; and
   a delivery device for delivering the needle and suture through a target tissue, including:
      a proximal jaw including a proximal recess extending through a distal surface thereof and a proximal retention mechanism for releasably engaging the first end of the needle in the proximal recess; and
      a distal jaw movably coupled to the proximal jaw such that the proximal and distal jaws are longitudinally movable relative to one another to receive a target tissue therebetween, the distal jaw including a distal recess extending through a proximal surface thereof and a distal retention mechanism for releasably engaging the second end of the needle in the distal recess, the proximal and distal jaws movable between a first state, in which the proximal retention mechanism is in a locked configuration to engage the needle received in the proximal recess and the distal retention mechanism is in an unlocked configuration so that the needle is freely slidable through the distal recess, and a second state, in which the proximal retention mechanism is in an unlocked configuration so that the needle is freely slidable through the proximal recess and the distal retention mechanism is in a locked configuration to engage a needle received in the distal recess,
   wherein the proximal retention mechanism includes a proximal wedge plate including an opening extending therethrough, the opening being substantially aligned with the proximal recess in the unlocked configuration and being angled with respect to the proximal recess in the locked configuration.

10. The system of claim 9, wherein at least one of the first end and the second end include a first groove extending thereabout for engaging a portion of the proximal retention mechanism in the locked configuration.

11. The system of claim 9, wherein the distal retention mechanism includes a form spring including an engaging portion extending into the distal recess in the locked configuration and being deformable thereoutof in the unlocked configuration.

12. The system of claim 9, wherein the distal retention mechanism includes a distal wedge plate including an opening extending therethrough, the opening being substantially aligned with the distal recess in the unlocked configuration and angled relative to the distal recess in the locked configuration.

13. A system for treating a tissue opening, comprising:
a needle extending from a first end to a second end;
a suture extending from a distal end connected to the needle between the first and second ends to a proximal end; and
a delivery device for delivering the needle and suture through a target tissue, including:
 a proximal jaw including a proximal recess extending through a distal surface thereof and a proximal retention mechanism for releasably engaging the first end of the needle in the proximal recess; and
 a distal jaw movably coupled to the proximal jaw such that the proximal and distal jaws are longitudinally movable relative to one another to receive a target tissue therebetween, the distal jaw including a distal recess extending through a proximal surface thereof and a distal retention mechanism for releasably engaging the second end of the needle in the distal recess, the proximal and distal jaws movable between a first state, in which the proximal retention mechanism is in a locked configuration to engage the needle received in the proximal recess and the distal retention mechanism is in an unlocked configuration so that the needle is freely slidable through the distal recess, and a second state, in which the proximal retention mechanism is in an unlocked configuration so that the needle is freely slidable through the proximal recess and the distal retention mechanism is in a locked configuration to engage a needle received in the distal recess,
wherein the distal retention mechanism includes a ball detent extending into the distal recess in the locked configuration and movable thereoutof in the unlocked configuration.

* * * * *